(12) United States Patent
Srinivasan et al.

(10) Patent No.: US 10,605,793 B2
(45) Date of Patent: Mar. 31, 2020

(54) AUTOMATED METHOD OF CALIBRATING A CHROMATOGRAPHY SYSTEM AND ANALYSIS OF A SAMPLE

(71) Applicant: DIONEX CORPORATION, Sunnyvale, CA (US)

(72) Inventors: Kannan Srinivasan, Tracy, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 214 days.

(21) Appl. No.: 15/716,308

(22) Filed: Sep. 26, 2017

(65) Prior Publication Data

US 2018/0024101 A1      Jan. 25, 2018

Related U.S. Application Data

(62) Division of application No. 14/490,527, filed on Sep. 18, 2014, now Pat. No. 9,804,136.

(51) Int. Cl.
*G01N 30/86* (2006.01)
*G01N 30/96* (2006.01)
*G01N 30/04* (2006.01)

(52) U.S. Cl.
CPC ..... *G01N 30/8668* (2013.01); *G01N 30/8675* (2013.01); *G01N 30/96* (2013.01); *G01N 2030/047* (2013.01)

(58) Field of Classification Search
CPC ......... G01N 2030/047; G01N 30/8668; G01N 30/867; G01N 30/96

USPC .................. 73/1.02, 23.41, 61.55
See application file for complete search history.

(56) References Cited

U.S. PATENT DOCUMENTS

| | | |
|---|---|---|
| 4,657,729 A | 4/1987 | Bunch et al. |
| 4,999,098 A | 3/1991 | Pohl et al. |
| 5,760,394 A | 6/1998 | Welle |
| 5,804,142 A | 9/1998 | Ito et al. |
| 5,905,192 A | 5/1999 | Wikfors et al. |
| 5,969,228 A | 10/1999 | Gorenstein |

(Continued)

FOREIGN PATENT DOCUMENTS

| | | |
|---|---|---|
| CN | 101226178 A | 7/2008 |
| CN | 101266233 B | 9/2008 |

(Continued)

OTHER PUBLICATIONS

European Union, The Commission of the European Communities. (2002). Commission Decision of Aug. 14, 2002implementing Council Directive 96/23/EC concerning the performance of analytical methods and the interpretation of results 2002/657/EC (pp. 1-27).

(Continued)

*Primary Examiner* — Daniel S Larkin
(74) *Attorney, Agent, or Firm* — Timothy J. Ohara

(57) ABSTRACT

An automated method of calibrating a chromatography system and analyzing a sample is described. The method includes forming diluted standard solutions that are injected into a chromatography column. The detected peaks can be identified based on a first predetermined calibration ratio associated with the standard solution. Once the chromatography system is calibrated, samples can be chromatographically analyzed where the measured peaks are identified and quantified in an automated manner.

8 Claims, 6 Drawing Sheets

(56) References Cited

U.S. PATENT DOCUMENTS

| | | | |
|---|---|---|---|
| 6,225,129 | B1 | 5/2001 | Liu et al. |
| 6,239,139 | B1 | 5/2001 | Kim et al. |
| 6,328,885 | B1 | 12/2001 | Srinivasan et al. |
| 6,544,484 | B1 | 4/2003 | Kaufman et al. |
| 6,568,245 | B2 | 5/2003 | Kaufman |
| 6,682,701 | B1 | 1/2004 | Liu et al. |
| 7,178,386 | B1 | 2/2007 | Gamble et al. |
| 7,329,346 | B2 | 2/2008 | Liu et al. |
| 8,043,507 | B2 | 10/2011 | Liu et al. |
| 8,415,168 | B2 | 4/2013 | Liu et al. |
| 2003/0110000 | A1 | 6/2003 | Quimby et al. |
| 2004/0258617 | A1 | 12/2004 | Weber et al. |
| 2006/0255258 | A1 | 11/2006 | Wang et al. |
| 2007/0112534 | A1 | 5/2007 | Jaeger |
| 2008/0072664 | A1 | 3/2008 | Hansen et al. |
| 2008/0110232 | A1 | 5/2008 | Miyagawa |
| 2008/0237457 | A1 | 10/2008 | Yamashita |
| 2009/0218238 | A1 | 9/2009 | Dasgupta et al. |
| 2010/0187414 | A1 | 7/2010 | Gorenstein et al. |
| 2010/0299078 | A1 | 11/2010 | Guieze |
| 2011/0184648 | A1 | 7/2011 | Gorenstein et al. |
| 2012/0156710 | A1 | 6/2012 | Nakayama et al. |
| 2014/0088923 | A1 | 3/2014 | Wang et al. |
| 2014/0156202 | A1 | 6/2014 | Floridia et al. |
| 2014/0260509 | A1 | 9/2014 | Pohl |

FOREIGN PATENT DOCUMENTS

| | | |
|---|---|---|
| CN | 101650347 B | 9/2009 |
| CN | 101738447 A | 6/2010 |
| CN | 102661939 B | 5/2012 |
| EP | 1752766 A1 | 2/2007 |
| EP | 2447712 A3 | 12/2012 |
| JP | 6276458 A | 4/1987 |
| JP | 09269319 A | 10/1997 |
| JP | 2006317198 A | 11/2006 |
| JP | 2007225420 A | 9/2007 |
| JP | 2011117815 A | 6/2011 |
| WO | 2005114220 A2 | 12/2005 |
| WO | WO2006110848 A2 | 10/2006 |
| WO | 2009058978 A1 | 5/2009 |
| WO | 2011012659 A2 | 2/2011 |
| WO | 2011155984 A1 | 12/2011 |
| WO | 2012170549 A1 | 12/2012 |
| WO | 2013044401 A1 | 4/2013 |
| WO | 2013181758 A1 | 12/2013 |

OTHER PUBLICATIONS

English abstract of JP 09-269319 pub. Oct. 1997 English abstract of JP 2007-225542 pub. Sep. 2007 English abstract of JP 2011-117815 pub. Jun. 2011 English abstract of JP 06-276458 pub. Apr. 1987.

Carell, "New promise in combinatorial chemistry: synthesis, characterization, and screening of small-molecule libraries in solution," Chemistry & Biology, 1995, vol. 2, No. 3, pp. 171-183.
Deport et al., "Comprehensive combinatory standard correction: A calibration method for handling instrumental drifts of gas chromatography—mass spectrometry systems," J of Chromatography A, 1116, 248-258, 2006.
Dolan, J.W. (Jun. 1, 2012). When Should an Internal Standard be Used? Retrieved Jul. 13, 2016, from http://www.chromatography online.com/when-should-internal-standard-be-used-0.
EPA Method 8000C, Rev 3, Mar. 2003, 66 pages.
Huang et al., "Determination of Pu in Spent Nuclear Fuel by Ion Chromatographic Separation-Peak Area Ratio Method," J. of Nuclear and Radiochemistry, 29(2), 85-89, 2007.
Instrumental Analysis (CEM 333) Resource Page, http://www.cem.msu.edu/~cem333/InternalStandard.html, downloaded 2013, 2 pages.
Johnson et al., "High-speed peak matching algorithm for retention time alignment of gas chromatographic data for chemometric analysis," J. of Chromatography A, vol. 996, No. 1-2, pp. 141-155, 2003.
Jones, "Making an HPLC Calibration work (Part 1)," Chromatography Focus, ILM, Oct. 1, 2009, pp. 103-105.
Khan et al., "A new method of analysis of peroxydisulfate using ion chromatography and its application to the simultaneous determination of peroxydisulfate and other common inorganic ions in a peroxydisulfate matrix," Journal of Chromatography A.
Li et al., "A Method of Fitting and Quick Resolution of Skewed and Overlapped Chromatographic Peaks," Chinese J. of Chromatography, vol. 10, No. 5, 251-254, 1992 (English abstract on last page).
Liang and Lucy, "Characterization of ion chromatography columns based on hydrophobicity and hydroxide eluent strength," Journal of Chromatography A, 1217, 8154-8160, 2010.
PowerPoint presentation, Internal Standard Calibration, http://www.azdhs.gov/lab/documents/license/resources/calibration-training/04-internal-standard-calib.pdf, website accessed Feb. 12, 2013.
Quantitative & Qualitative HPLC, Jan. 1, 2014, retrieved from the Internet: URL: http://www.chromacademy.com/lms/sco9/Theory_Of-HPLC-Quantitative_and_Qualitative_HPLC.pdf [retrieved on Sep. 8, 2014].
Restek, Material Safety Data Sheet Sulfur Simulated Distillation Standard, http://www.restek.com/documentation/msds/33049_useng.pdf, Jul. 24, 2008.
Sequant, "A Practical Guide to Ion Chromatography: An introduction and troubleshooting manual," The Nest Group, Inc., 1998-2007, 23 pages.
Smiley, Thesis entitled "Chemi-Code: An Innovative Method for Wood Product Tracking," The University of British Columbia, Apr. 2008, 108 pages.
Understanding Your Agilent ChemStation, Agilent User Manual, Jul. 1, 2009, pp. 130-158.
U.S. Appl. No. 13/834,883, filed Mar. 15, 2013; spec, claims, abstract, drawings.
Vanatta et al., "Ion-chromatographic quantitation of fluoride and acetate—Statistical comparison of calibration curves from two similar eluents," J. of Chrom. A, 804, 123-129, 1998.

AUTOMATED METHOD OF CALIBRATING A CHROMATOGRAPHY SYSTEM AND ANALYSIS OF A SAMPLE

CROSS REFERENCE TO RELATED APPLICATIONS

This is a divisional application and claims the priority benefit of application Ser. No. 14/490,527 filed on Sep. 18, 2014 now U.S. Pat. No. 9,804,136, the disclosure of which is incorporated herein by reference.

BACKGROUND

Chromatography is a widely used analytical technique for the chemical analysis and separation of molecules. Chromatography involves the separation of one or more analyte species from matrix components present in a sample. The analytes and matrix components have an affinity for the stationary phase. In ion exchange chromatography, the stationary phase includes ionic moieties that ideally will bind to the charged analytes with varying levels of affinity. An eluent is percolated through the stationary phase and competes with the analyte and any matrix components for binding to the ionic moieties. The eluent is a term used to describe a liquid or buffer solution that is pumped into a chromatography column. During this competition, the analyte and any matrix components will separate from each other by eluting off of the stationary phase as a function of time and then be subsequently detected at a detector. Examples of some typical detectors are a conductivity detector, a UV-VIS spectrophotometer, and a mass spectrometer.

Chromatography typically requires a calibration process to both identify the analyte of interest and quantitate the amount of analyte. A standard solution is often used as part of a calibration process for determining the chemical identity of the chromatographic peaks of a sample solution. The standard solution can have one or more types of analytes where each one is at a known predetermined concentration. A chromatogram of the standard solution will provide the retention times, peak heights, and peak areas for the analytes in the standard solution. Such information acquired with the standard solution can be compared to the chromatogram of a sample solution to determine the chemical identity and concentration of the components in the sample solution. For instance, the peak retention times of the standard solution can be correlated with the peak retention time of the sample solution to determine the chemical identity of the peaks of the sample chromatogram. The chemical identities of the standard components are verified by injecting individual pure components of the standard and these identities are established by the peak retention times.

In regards to quantitation, several dilutions of the standard solution can be prepared manually and analyzed chromatographically. It should be noted that user error can be significant when manually preparing diluted standard solutions. The measured peak areas or peak heights from the diluted standards can then be used to calculate calibration slopes and intercepts for each of the analytes in the standard solution. A sample containing one or more analytes can be analyzed chromatographically to measure one or more peak areas corresponding to analytes. These peak areas can be used to quantitate analyte concentrations based on the corresponding calibration slopes and intercepts. Applicant believes that there are several problems with calibration and sample analysis processes in that the process needs to be more automated in analyte identification, diluting standard solution for calibration with reduced user input, determining proper calibration concentration ranges, and automated sample concentration calculations.

SUMMARY

In a first method embodiment of calibrating a chromatography system, it includes an automatic identification step based on a first predetermined calibrant ratio and another automatic identification step based on peak retention times, and a first and second analyte time intervals. This first method is well suited for calibrating analyte ions that are strongly dissociated, weakly dissociated, and combinations thereof.

The first method includes forming a first diluted standard solution by mixing a standard material and a diluent. The first diluted standard solution includes a first analyte having a first diluted calibrant concentration, and a second analyte having a second diluted calibrant concentration, in which the first diluted standard solution is configured to have a first predetermined calibrant ratio. The first diluted standard solution is injected into a chromatographic separator. The first diluted standard solution is separated in the chromatographic separator. A first peak and a second peak are measured with a detector. The first peak and second peak have a first retention time and a second retention time, respectively. Automatically identifying whether the first peak corresponds to the first analyte or the second analyte, and whether the second peak corresponds to the first analyte or the second analyte, based on either an area or a height of the first peak and the second peak, and the first predetermined calibrant ratio. A first analyte time interval is assigned based on one of the first retention time and second retention time that corresponds to the first analyte. A second analyte time interval is assigned based on one of the first retention time and second retention time that corresponds to the second analyte. A second diluted standard solution is formed by mixing the standard material and the diluent. The second diluted standard solution includes the first analyte having a third diluted calibrant concentration, and the second analyte having a fourth diluted calibrant concentration. The second diluted standard solution is injected into the chromatographic separator. Next, the second diluted standard solution separated in the chromatographic separator. A third peak and a fourth peak are measured with the detector. The third peak and the fourth peak have a third retention time and a fourth retention time, respectively. Automatically identifying that the third peak corresponds to the first analyte where the third retention time falls within the first analyte time interval or the second analyte where the third retention time falls within the second analyte time interval. Automatically identifying that the fourth peak corresponds to the first analyte where the fourth retention time falls within the first analyte time interval or the second analyte where the fourth retention time falls within the second analyte time interval. Automatically calculating a first calibration equation for the first analyte based on an area or a height of two of the automatically identified peaks that correspond to the first analyte, the two peaks selected from the group consisting of the first peak, the second peak, the third peak, and the fourth peak; the first and third diluted calibrant concentrations. Automatically calculating a second calibration equation for the second analyte based on an area or a height of two of the automatically identified peaks that correspond to the second analyte, the two peaks selected from the group consisting of the first peak, the second peak, the third peak, and the fourth peak; and the second and fourth diluted calibrant concentrations.

In a second method embodiment of calibrating a chromatography system, it includes at least two automatic identifications step based on a first predetermined calibrant ratio. This second method is well suited for calibrating analyte ions that are strongly dissociated.

The second method includes forming a first diluted standard solution by mixing a standard material and a diluent. The first diluted standard solution includes a first analyte having a first diluted calibrant concentration, and a second analyte having a second diluted calibrant concentration, in which the first diluted standard solution is configured to have a first predetermined calibrant ratio. The first diluted standard solution is injected into a chromatographic separator. The first diluted standard solution is separated in the chromatographic separator. A first peak and a second peak are measured with a detector. The first peak and second peak have a first retention time and a second retention time, respectively. Automatically identifying whether the first peak corresponds to the first analyte or the second analyte, and whether the second peak corresponds to the first analyte or the second analyte, based on either an area or a height of the first peak and the second peak, and the first predetermined calibrant ratio. A second diluted standard solution is formed by mixing the standard material and the diluent. The second diluted standard solution includes the first analyte having a third diluted calibrant concentration, and the second analyte having a fourth diluted calibrant concentration. The second diluted standard solution is injected into the chromatographic separator. Next, the second diluted standard solution separated in the chromatographic separator. A third peak and a fourth peak are measured with the detector. The third peak and the fourth peak have a third retention time and a fourth retention time, respectively. Automatically identifying whether the third peak corresponds to the first analyte or the second analyte, and whether the fourth peak corresponds to the first analyte or the second analyte, based on either an area or a height of the third peak and the fourth peak, and the first predetermined calibrant ratio. Automatically calculating a first calibration equation for the first analyte based on an area or a height of two of the automatically identified peaks that correspond to the first analyte, the two peaks selected from the group consisting of the first peak, the second peak, the third peak, and the fourth peak; the first and third diluted calibrant concentrations. Automatically calculating a second calibration equation for the second analyte based on an area or a height of two of the automatically identified peaks that correspond to the second analyte, the two peaks selected from the group consisting of the first peak, the second peak, the third peak, and the fourth peak; and the second and fourth diluted calibrant concentrations.

In regards to the first and second method, the first calibration equation can include a first calibration slope and a first y-intercept and the second calibration equation can include a second calibration slope and second y-intercept.

In regards to the first and second method, the first and second calibration equations can be in a polynomial form. The calculations for the polynomial equations can require a third calibration point. This method includes forming a third diluted standard solution by mixing a standard material and a diluent. The third diluted standard solution includes the first analyte having a fifth diluted calibrant concentration, and the second analyte having a sixth diluted calibrant concentration. The third diluted standard solution is injected into the chromatographic separator. The third diluted standard solution is separated in the chromatographic separator. A fifth peak and a sixth peak are measured with the detector. The fifth peak and the sixth peak have a fifth retention time and a sixth retention time, respectively. Automatically identifying that the fifth peak corresponds to the first analyte where the fifth retention time falls within the first analyte time interval or the second analyte where the fifth retention time falls within the second analyte time interval. Automatically identifying that the sixth peak corresponds to the first analyte where the sixth retention time falls within the first analyte time interval or the second analyte where the sixth retention time falls within the second analyte time interval. Automatically calculating the first calibration equation for the first analyte based on an area or a height of three of the automatically identified peaks that correspond to the first analyte, the three peaks selected from the group consisting of the first peak, the second peak, the third peak, the fourth peak, the fifth peak, and the sixth peak, and the first, third, and fifth diluted calibrant concentrations. Automatically calculating a second calibration equation for the second analyte based on an area or a height of three of the automatically identified peaks that correspond to the second analyte, the three peaks selected from the group consisting of the first peak, the second peak, the third peak, the fourth peak, the fifth peak, and the sixth peak, and the second, fourth, and sixth diluted calibrant concentrations. The first calibration equation includes a first polynomial equation, and the second calibration equation includes a second polynomial equation. More particularly, the first polynomial equation can be a first quadratic equation and the second polynomial equation can be a second quadratic equation.

In regards to any of the above methods, the first and second diluted solutions can be prepared using one or more pumps where the standard material includes a standard solution. The forming of the first diluted standard solution includes pumping a first aliquot of the standard solution and a second aliquot of the diluent into the junction. The standard solution includes the first analyte having a first calibrant concentration, and the second analyte having a second calibrant concentration. The first aliquot and the second aliquot can be mixed to form the first diluted standard solution. The forming of the second diluted standard solution includes pumping a third aliquot of the standard solution and a fourth aliquot of the diluent into the junction. The third aliquot and fourth aliquot can be mixed to form the second diluted standard solution. In an embodiment, the pumps can be syringe pumps.

In regards to any of the above methods, a user can input a concentration range of expected analyte concentrations that includes a lower analyte concentration and an upper analyte concentration for a particular analyte. In turn, this method can perform a seamless calibration process that accounts for a user inputted analyte concentration range to ensure that the diluted calibrant concentrations span a range similar to the range of expected analyte concentrations. A first concentration range for the first analyte can be received before forming the first diluted standard solution and the second diluted standard solution. The first concentration range can include a lower first analyte concentration and an upper first analyte concentration. Automatically calculating the first diluted calibrant concentration based on the upper first analyte concentration. Automatically setting a first flow rate or a first pump duration time for the first aliquot and a second flow rate or a second pump duration time for the second aliquot to form the automatically calculated first diluted calibrant concentration. Automatically calculating the third diluted calibrant concentration based on the lower first analyte concentration. Automatically setting a third flow rate or a third pump duration time for the third aliquot and a fourth flow rate or a fourth pump duration time for the fourth aliquot to form the automatically calculated third diluted calibrant concentration.

A sample containing a first analyte can be analyzed after the chromatography system has been calibrated with any of the above methods. A first sample analysis method includes injecting a first sample into the chromatographic separator where the first sample includes at least a first analyte. The first sample is separated in the chromatographic separator. A seventh peak is measured with the detector that has a seventh retention time. Automatically identifying that the seventh peak corresponds to the first analyte where the seventh retention time falls within the first analyte time interval. Automatically calculating a first analyte concentration of the first sample based on an area or a height of the seventh peak and the first calibration equation.

In regards to the first sample analysis methods, a feedback control method can be implemented when the automatically calculated analyte concentration is too low to be effectively analyzed with present calibration parameter. As a result, a recalibration process can be automatically triggered when such a low analyte concentration is measured. This method includes calculating a seventh diluted calibrant concentration for the first analyte is that is less than the automatically calculated first analyte concentration when the automatically calculated first analyte concentration is less than a lower first analyte concentration of a first concentration range. A fourth diluted standard solution is formed by mixing the standard solution and the diluent. The fourth diluted standard solution includes a first analyte having the seventh diluted calibrant concentration. The fourth diluted standard solution is injected into the chromatographic separator. The fourth diluted standard solution is separated in the chromatographic separator. An eighth peak is measured with the detector that has an eighth retention time. Automatically identifying that the eighth peak corresponds to the first analyte where the eighth retention time falls within the first analyte time interval. Automatically calculating an adjusted first calibration equation for the first analyte based on an area or a height of the eighth peak and at least one peak of the first, second, third, and fourth peaks that corresponds to the first analyte, and the seventh diluted calibrant concentration and at least one of the first, second, third, and fourth diluted calibrant concentrations that corresponds to the first analyte.

In regards to the first sample analysis method and the above feedback control method, another feedback control method can be implemented when the automatically calculated analyte concentration is too high to be effectively analyzed with present calibration parameter. As a result, a recalibration process can be automatically triggered when such a high analyte concentration is measured. This method includes calculating an eighth diluted calibrant concentration for the first analyte is that is greater than the automatically calculated first analyte concentration when the automatically calculated first analyte concentration is greater than an upper first analyte concentration of a first concentration range. A fifth diluted standard solution is formed by mixing the standard solution and the diluent. The fifth diluted standard solution includes a first analyte having the eighth diluted calibrant concentration. The fifth diluted standard solution is injected into the chromatographic separator. The fifth diluted standard solution is separated in the chromatographic separator. A ninth peak is measured with the detector that has a ninth retention time. Automatically identifying that the ninth peak corresponds to the first analyte where the ninth retention time falls within the first analyte time interval. Automatically calculating an adjusted first calibration equation for the first analyte based on an area or a height of the ninth peak and at least one peak of the first, second, third, and fourth peaks that corresponds to the first analyte, and the eighth diluted calibrant concentration and at least one of the first, second, third and fourth diluted calibrant concentrations that corresponds to the first analyte.

A sample containing a first analyte and a second analyte can be analyzed after the chromatography system has been calibrated with any of the above methods. A second sample analysis method includes injecting a first sample into the chromatographic separator. The first sample includes a first analyte and a second analyte. The first sample is separated in the chromatographic separator. An eleventh peak and a tenth peak is measured with the detector. The eleventh peak has an eleventh retention time and the tenth peak has a tenth retention time. Automatically identifying that the eleventh peak corresponds to the first analyte where the eleventh retention time falls within the first analyte time interval or the eleventh peak corresponds to the second analyte where the eleventh retention time falls within the second analyte time interval. Automatically identifying that the tenth peak corresponds to the first analyte where the tenth retention time falls within the first analyte time interval or the tenth peak corresponds to the second analyte where the tenth retention time falls within the second analyte time interval. Automatically calculating a first analyte concentration of the first sample based on an area or a height of one of the automatically identified peaks selected from the group consisting of the eleventh peak and the tenth peak that corresponds to the first analyte and the first calibration equation. Automatically calculating a second analyte concentration of the first sample based on an area or a height of one of the automatically identified peaks selected from the group consisting of the eleventh peak and the tenth peak that corresponds to the second analyte and the second calibration equation.

In regards to any of the above methods, the first analyte time interval has a first upper limit and a first lower limit. The first upper limit being one of the first retention time and the second retention time corresponding to the first analyte plus a first predetermined proportion multiplied by one of the first retention time and the second retention time corresponding to the first analyte. The first lower limit being one of the third retention time and the fourth retention time corresponding to the first analyte minus a first predetermined proportion multiplied by one of the third retention time and the fourth retention time corresponding to the first analyte. The first predetermined proportion may range from about 0.05 to about 0.2.

In regards to any of the above methods, the second analyte time interval has a second upper limit and a second lower limit. The second upper limit being one of the first retention time and the second retention time corresponding to the second analyte plus a first predetermined proportion multiplied by one of the first retention time and the second retention time corresponding to the second analyte. The first lower limit being one of the third retention time and the fourth retention time corresponding to the second analyte minus a first predetermined proportion multiplied by one of the third retention time and the fourth retention time corresponding to the second analyte. The second predetermined proportion may range from about 0.05 to about 0.2.

In regards to any of the above methods, the junction may include a T-junction.

In regards to any of the above methods, the mixing may occurs in a mixing chamber downstream of the T-junction.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

In a method embodiment of calibration, a standard solution can be run in a chromatographic instrument that produces a predetermined ratio of at least two peaks at a predetermined (concentration) level. The chromatogram from this injection is used to identify the peaks. The retention times required for future identification of the peaks at that location with the appropriate retention time window can be assigned. Next, a series of diluted standards solution can be prepared and run in a chromatographic instrument where the retention time window is used to detect and identify the peaks in an automated fashion. The diluted standard solution is identified based on retention times and not the predetermined ratio. Under certain conditions where one analyte is a fully dissociated acid and another analyte is a weakly dissociated analyte, a diluted standard solution may not have a constant predetermined ratio of two peaks compared to the standard solution (undiluted). In the above method, the calibration process accounts for difficulties calibrating and analyzing samples including weakly dissociated species and strongly dissociated species. It should be noted that conductivity detectors can have a linear response for strongly dissociated species and a curved response (e.g., quadratic) for weakly dissociated species.

Figure 1:
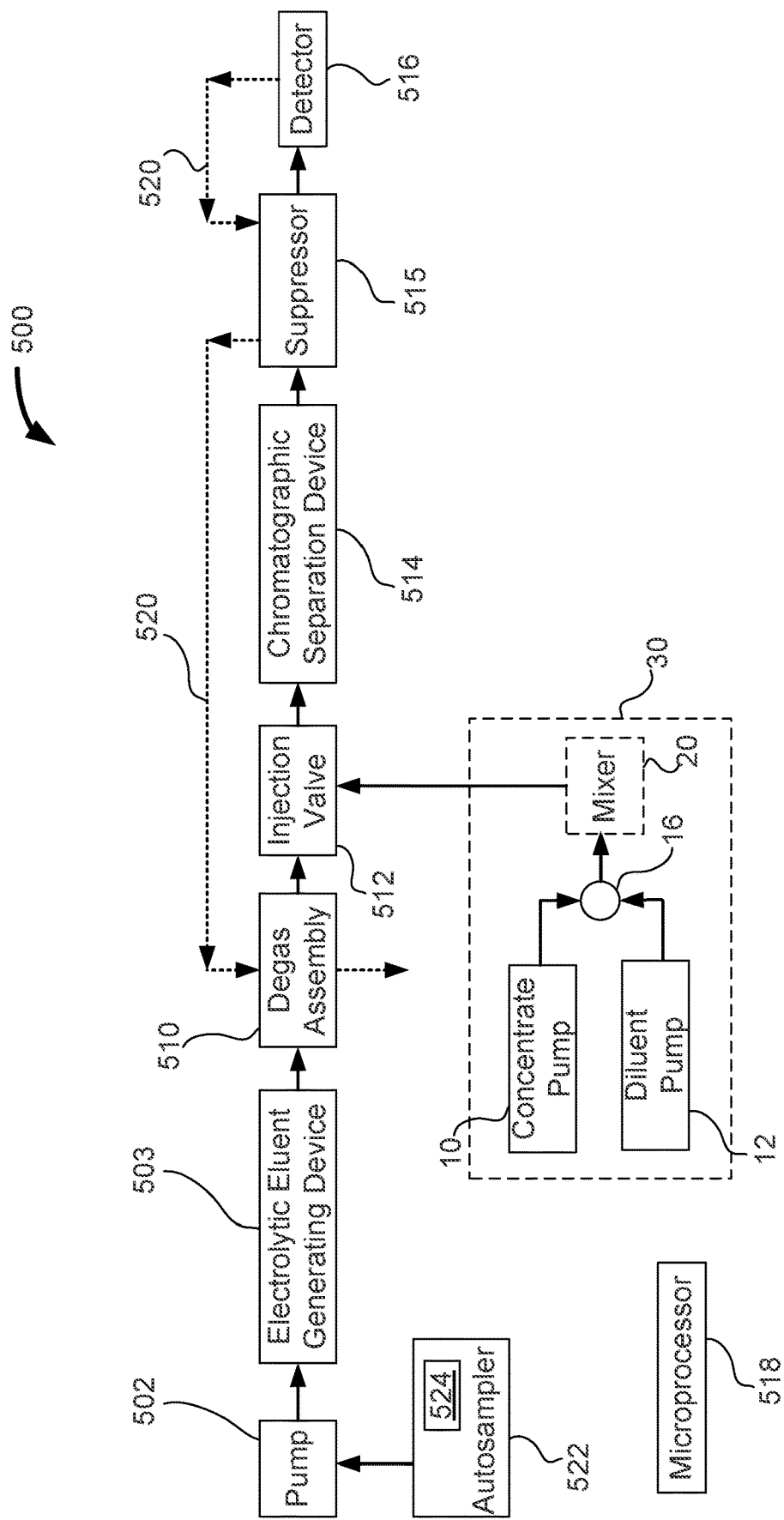
FIG. 1 illustrates an embodiment of a chromatography system suitable for use with the chromatographic methods described herein.

The following describes a general chromatography system suitable for use with the methods of calibration and sample analysis described herein. FIG. 1 illustrates an embodiment of an ion chromatography system 500 that includes an autosampler 522, a pump 502, an electrolytic eluent generating device 503, a degas assembly 510, an injection valve 512, a chromatographic separation device 514, an optional suppressor 515, a detector 516, automated standards dilution system 30, a microprocessor 518, and a reader 524 such as an RFID reader. A recycle line 520 may be used to transfer the liquid from an output of detector 516 to a regenerant portion of suppressor 515, and an inlet of degas assembly 510. Reader 524 may include a bar code reader or a contact mechanism for reading data using wires.

Pump 502 can be configured to pump a liquid from a liquid source and be fluidically connected to electrolytic eluent generating device 503. Electrolytic eluent generating device 503 is configured to generate an eluent such as for example KOH or methanesulfonic acid. Details regarding electrolytic eluent generating devices can be found in U.S. Pat. Nos. 6,225,129 and 6,682,701, which are hereby incorporated by reference herein. In an embodiment, a residual gas may be carbon dioxide, hydrogen, and oxygen. The gas can be swept out of degas assembly 510 using a recycled liquid via a recycle line 520 that is downstream of detector 516. Injection valve 512 can be used to inject an aliquot of a liquid sample into an eluent stream. Chromatographic separation device 514 can be used to separate various matrix components present in the liquid sample from the analytes of interest. An output of chromatographic separation device 514 can be fluidically connected to suppressor 515, and then to detector 516 to measure the presence of the separated chemical constituents of the liquid sample.

Suppressor 515 is a device used in ion chromatography to remove the eluent and sample counterions and replace them with regenerant ions. As a result, the eluent is converted a weakly dissociated form prior to entering the detector. The suppressor allows analyte ions to be detected with a conductivity detector with a low background. Furthermore, the analytes can be converted to the more conductive acid or base form, which enhances the signal, particularly for fully dissociated species. Detail regarding suppressors can be found in U.S. Pat. Nos. 4,999,098; 6,328,885; and 8,415,168 which are hereby fully incorporated by reference herein.

Detector 516 may be in the form of ultraviolet-visible spectrometer, a fluorescence spectrometer, an electrochemical detector, a conductometric detector, a charge detector, or a combination thereof. Details regarding the charge detector that is based on a charged barrier and two electrodes can be found in US Pre-Grant Publication No. 20090218238, which is hereby fully incorporated by reference herein. For the situation where recycle line 520 is not needed, detector 516 may also be in the form of a mass spectrometer or a charged aerosol detector. The charged aerosol detector nebulizes the effluent flow and creates charged particles that can be measured as a current proportional to the analyte concentration. Details regarding the charged aerosol detector can be found in U.S. Pat. Nos. 6,544,484; and 6,568,245, which are hereby fully incorporated by reference herein.

An electronic circuit may include microprocessor 518 and a memory portion. Microprocessor 518 can be used to control the operation of chromatography system 500. Microprocessor 518 may either be integrated into chromatography system 500 or be part of a personal computer that communicates with chromatography system 500. Microprocessor 518 may be configured to communicate with and control one or more components of chromatography system such as autosampler 522, reader 524, pump 502, electrolytic eluent generating device 503, injection valve 512, and detector 516. Note that chromatography system 500 is a particular machine used to analyze standard solutions and sample solutions to identify chemical constituents and the associated concentration values.

Figure 2:
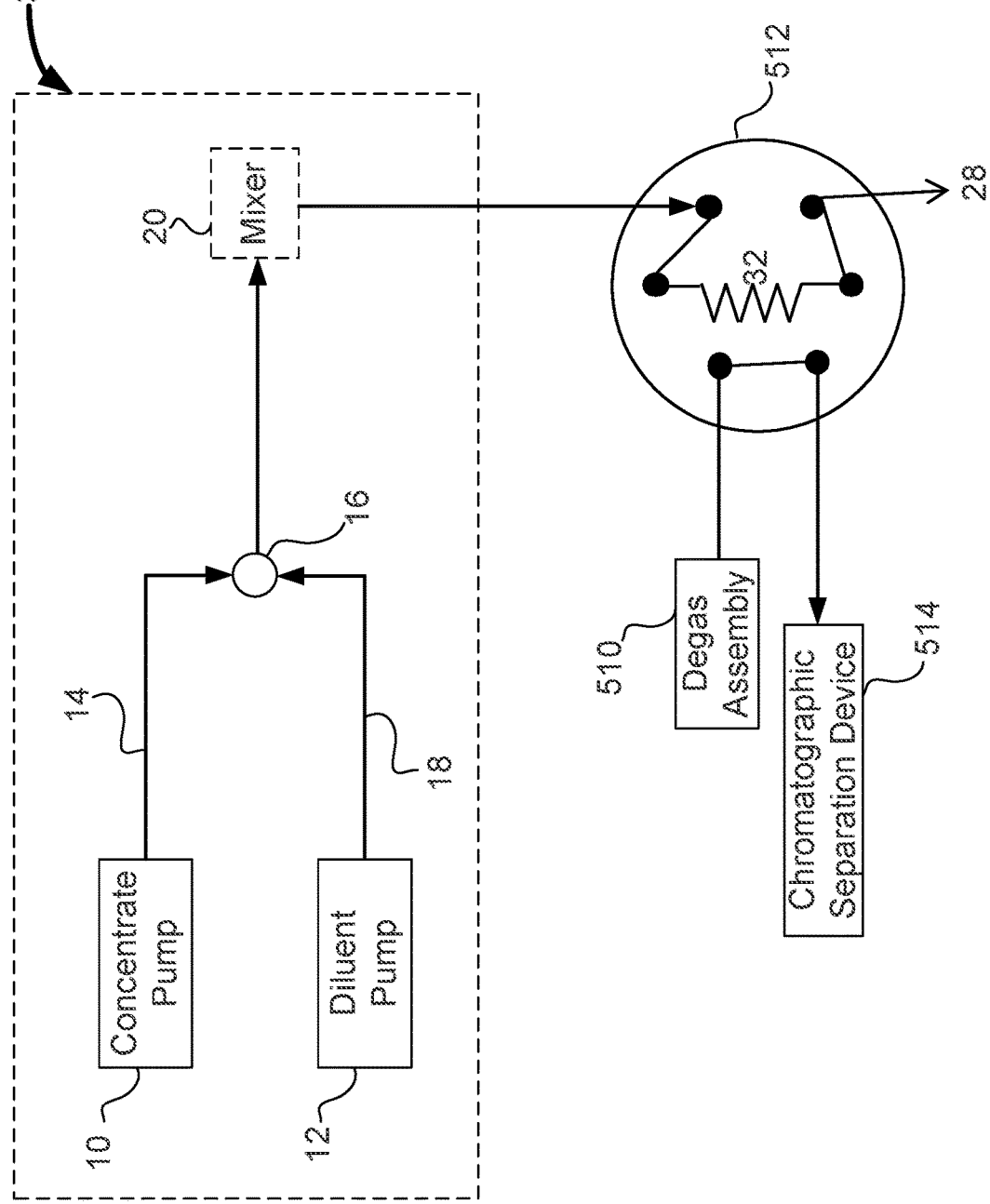
FIG. 2 illustrates a simplified schematic of an automated standards dilution system in a load position that is in accordance with the chromatography system of FIG. 1.
Figure 3:
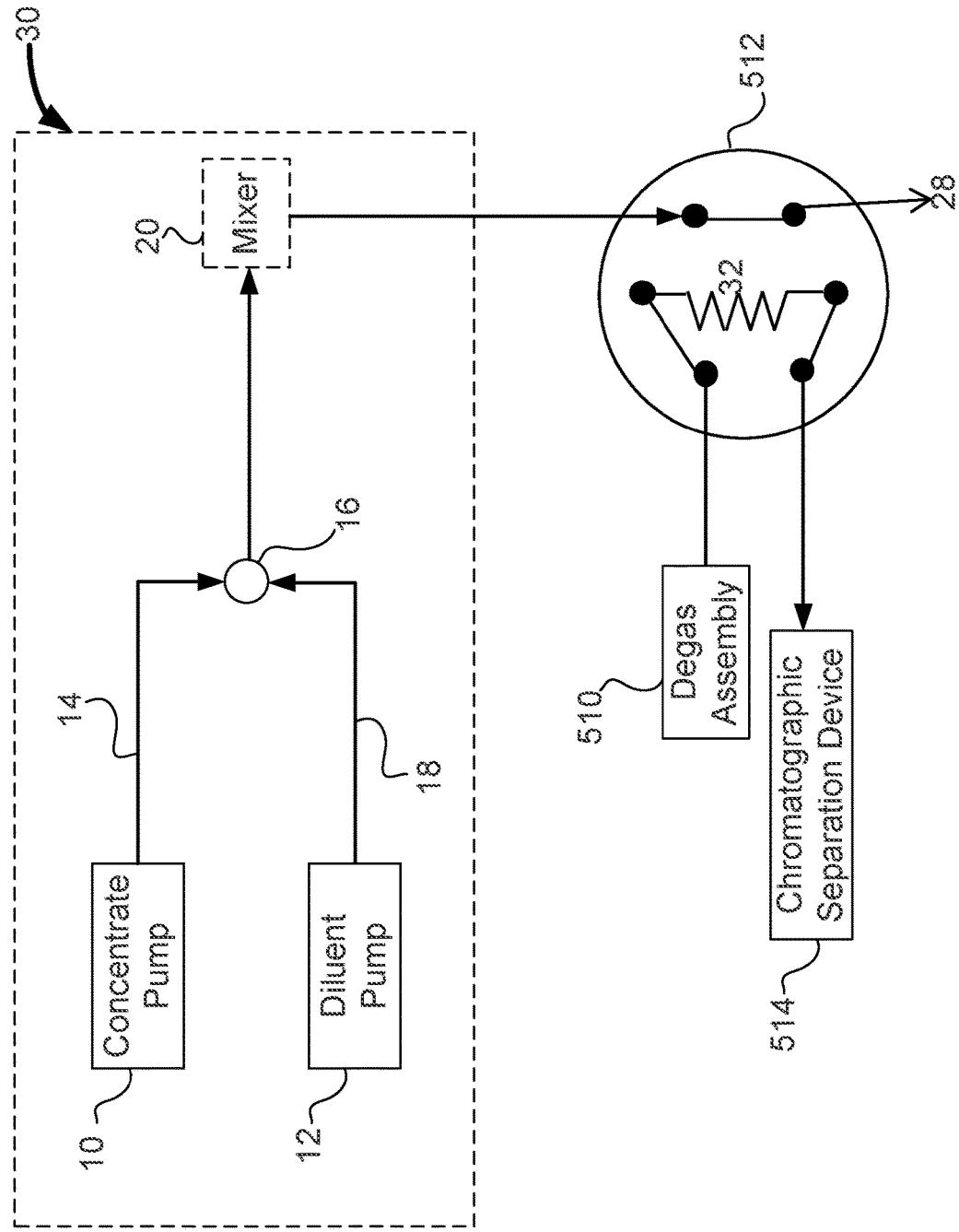
FIG. 3 illustrates a simplified schematic of the automated standards dilution system in an inject position that is in accordance with the chromatography system of FIG. 1.

An automated standards dilution system can be used to create a variety of dilutions of a standard solution. Standard solutions may have one or more analytes where each analyte is at a predetermined concentration. As illustrated in FIGS. 1 to 3, automated standards dilution system 30 includes a concentrate pump 10, a diluent pump 12, a junction 16, and an optional mixer 20. The output of concentrate pump 10 and diluent pump 12 can be inputted into junction 16 via tubings 14 and 18, respectively, to combine the two liquids, as illustrated in FIGS. 2 and 3. Junction 16 may be in the form of a "tee" junction (i.e. T-junction). Where additional mixing is needed in addition to that provided by junction 16, an optional mixer 20 may be used before injecting into injection valve 512. After the combination of liquids from concentrate pump 10 and diluent pump 12, the mixed liquid can flow to injection valve 512. As illustrated in FIGS. 2 and 3, injection valve 512 is in the form of a six-port injection valve. The mixed liquid containing the standard solution is loaded onto a sample loop 32 with the excess standard solution going to a waste reservoir 28 in the load position as illustrated in FIG. 2. The sample loop can be injected towards chromatographic separation when valve 512 is changed to the inject position.

In an embodiment, concentrate pump 10 can pump a standard solution that has a relatively high concentration of analytes. An example of a concentrated standard is the combined five anion standard containing 20 mg/L fluoride, 30 mg/L chloride, 100 mg/L nitrate, 150 mg/L phosphate, and 150 mg/L sulfate (commercially available from Thermo Scientific Dionex part number 057590, Sunnyvale, Calif., USA). Diluent pump 12 can pump a diluent such as, for example, deionized water. For example a concentrated standard mixture of five anions can be pumped in at a flow rate of 1 µL/min. The diluent pump can be operated at a flow rate of 99 µL/min to produce a net flow of a diluted standard solution at 100 µL/min. The concentration of the diluted standard solution in this case would be a 100 fold dilution.

An optional mixer column 20 can be used to mix the standards well before injecting into a loop 32 that is installed in a six port injection valve 24. The injection valve has an inlet that is fluidically connected to pump 502, and with one or more of the following devices, which are degas assembly 510, electrolytic eluent generating device 503, and autosampler 522. The injection valve has an outlet that is fluidically connected with chromatographic separation device 514, detector 516, and optional suppressor 515.

The flow rate of concentrate pump 10 and diluent pump 12 can be varied so that different dilutions of the standard solution can be generated. In the load position of injection valve 512, loop 32 is loaded with the diluted standard solution as illustrated in FIG. 2. In the inject position shown in FIG. 2, the contents of loop 32 are injected into an ion chromatograph for analysis. The pumps 10 and 12 can be syringe pumps that can be driven using a single drive system. The pumps 10 and 12 can also be in the form of a simple proportioning valve setup that allows proportioning of the concentrate and diluent at different ratios. Automated standards dilution system 30 can be controlled by a software interface using microprocessor 518.

An automated calibration routine is described that combines the steps of a) calibrant generation via automated dilution, and b) identification based on preset response ratios. This automated calibration routine is configured to require a reduced amount user intervention or no user intervention. After calibrating a system, a method of using a chromatography system may be used to a) identify peaks of interest based on retention time b) provide a measured analyte response based on a concentration curve. In order to get an accurate quantitation, one or more levels of the standard solutions are chromatographically analyzed during calibration. Standard solutions may be prepared in an offline fashion, diluted, and injected into the system for the purpose of calibration. Any errors in dilution can impact the calibration curve and hence cause the quantitation to be less accurate.

Figure 4:
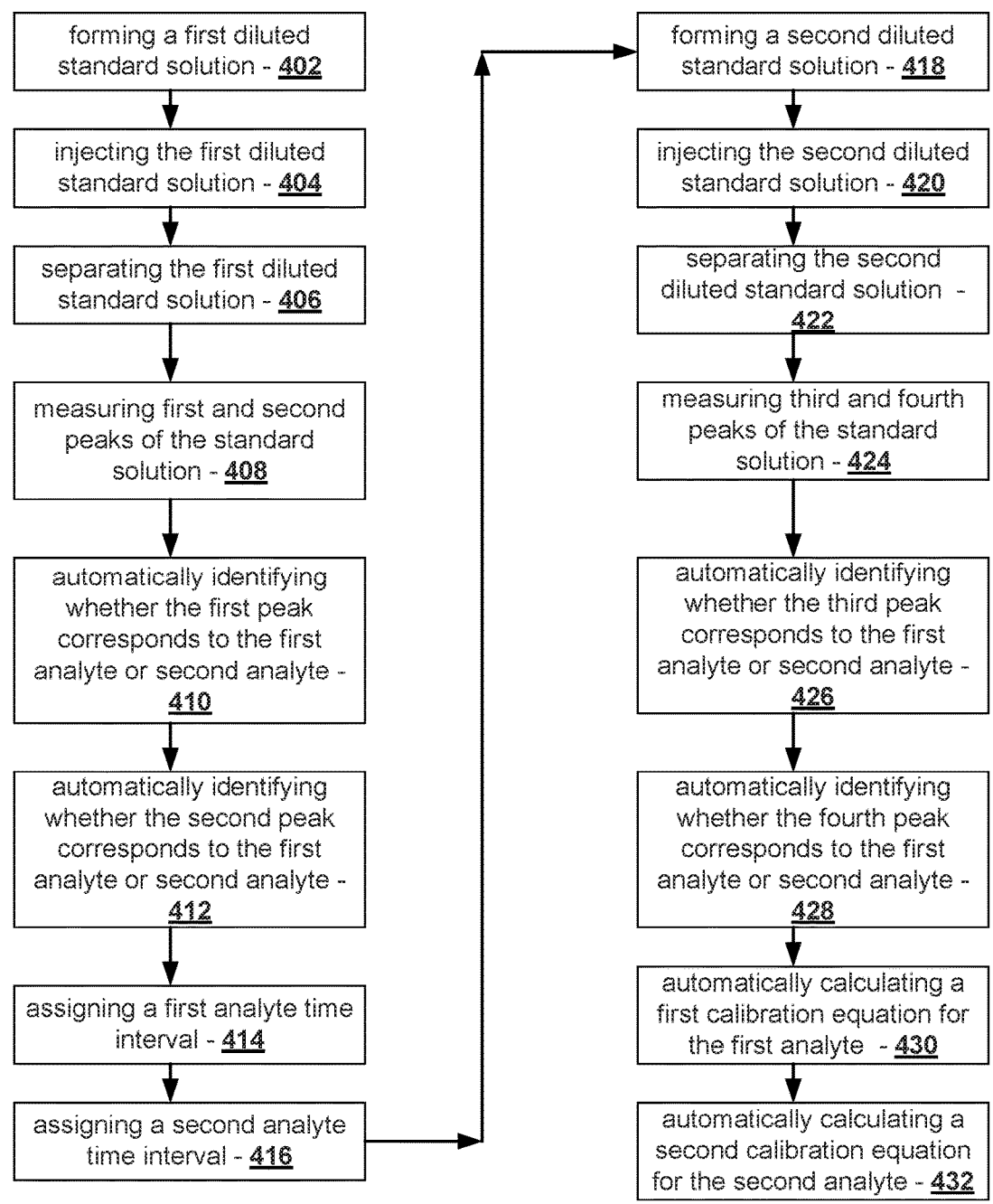
FIG. 4 is a flow chart illustrating an automatic method of calibrating a chromatography system with diluted standard solutions.

A method of using an analytical system typically includes a calibration step and a sample analysis step. The following will describe a method of calibrating a chromatography system in more detail. FIG. 4 is a flow chart illustrating an automatic method 400 of calibrating a chromatography system with a standard solution. Method 400 may include forming a first diluted standard solution (step 402), injecting the first diluted standard solution (step 404), separating the first diluted standard solution (step 406), measuring first and second peaks of the standard solution (step 408), automatically identifying whether the first peak corresponds to the first analyte or second analyte (step 410), automatically identifying whether the second peak corresponds to the first analyte or second analyte (step 412), assigning a first analyte time interval (step 414), assigning a second analyte time interval (step 416), forming a second diluted standard solution (step 418), injecting the second diluted standard solution (step 420), separating the second diluted standard solution (step 422), measuring third and fourth peaks of the standard solution (step 424), automatically identifying whether the third peak corresponds to the first analyte or second analyte (step 426), automatically identifying whether the fourth peak corresponds to the first analyte or second analyte (step 428), automatically calculating a first calibration equation for the first analyte (step 430), and automatically calculating a second calibration equation for the second analyte (step 432).

In step 402, a first diluted standard solution is formed by mixing a standard material and a diluent. The first diluted standard solution may include a first analyte having a first diluted calibrant concentration and a second analyte having a second diluted calibrant concentration. The first diluted standard solution is configured to have a first predetermined calibrant ratio.

A standard material may be in the form of a concentrated liquid solution or a solid compound. In an embodiment, the standard material can be a standard solution and contains a plurality of analytes. For example, the standard solution may be a five anion standard containing fluoride, chloride, nitrate, phosphate, and sulfate. The solid compound can be an aggregate of analyte salts. In an embodiment, a manual process can be implemented to prepare a combination of solid analytes for the standard material. The diluent may be a liquid solution such as deionized water. The standards can be prepared on a weight by weight or volume by volume basis.

The first predetermined calibrant ratio can be a numerical value assigned to the first diluted standard solution. The first predetermined calibrant ratio can be based on a ratio of a peak area corresponding to a first analyte and a peak area corresponding to the second analyte. Alternatively, a peak height can be used instead of peak area where the first predetermined calibrant ratio is based on a ratio of a peak height corresponding to a first analyte and a peak height corresponding to the second analyte.

Prior to the calibration process 400, the standard material can be characterized using chromatography to establish a predetermined calibrant ratio. For example, a standard solution can include fluoride and chloride where the respective concentrations are adjusted so that the measured peak areas on a conductivity detector have a peak area ratio of 2:1, which corresponds to the first predetermined calibrant ratio. In this example, the fluoride has an approximately two-fold higher concentration than chloride. Under certain circumstances, the measured peak areas are not always proportional based on concentration values because the sensitivity of fluoride and chloride may be different on a conductivity detector. If this were case, the concentrations of fluoride and chloride would be adjusted until the desired peak area ratio was measured. It should be noted that method 400 is not limited to one predetermined calibrant ratio and that multiple predetermined calibrant ratios can be used for standard solutions containing multiple analytes. For simplicity, method 400 will be described with two analytes and one predetermined calibrant ratio. It should be noted that method 400 is not limited to only two analytes and that one having ordinary skill in the art would be able to apply method 400 to more than two analytes.

The following will describe an automated method of preparing a diluted standard solution where the standard material is a standard solution. The forming of the first diluted standard solution includes pumping a first aliquot of the standard solution into a junction and pumping a second aliquot of a diluent into the junction. The first aliquot and the second aliquot can be mixed in the junction to form the first diluted standard solution. The junction may be in the form of a tee junction where the first aliquot and second aliquot are inputted into two respective inlets of the tee junction and outputted as a mixture. A mixer may be used downstream of the tee junction for certain circumstances where more mixing may be needed. In an embodiment, two syringe pumps may be used to pump the first and second aliquots into the junction. The pumping of the two aliquots may occur simultaneously or may occur separately in time. The aliquots can be provided by a flowing stream into the junction or a volume of liquid. Where the two pumps operate simultaneously, the flow rates of the two pumps can be set so that the appropriate magnitudes of the two aliquots are generated to provide the diluted standard solution. Where the two pumps do not operate simultaneously, the flow rates of the two pumps can be set by the outputted volume so that the appropriate magnitudes of the two aliquots are generated to provide the diluted standard solution.

Once the first diluted standard solution is prepared, it is injected into a chromatographic separator in step 404. In an embodiment, the chromatographic separator may be an ion exchange column and the analytes may be anions. The first diluted standard solution is separated in the chromatographic separator in step 406. A first peak and a second peak can be measured with a detector in step 408. It should be noted that the separation of the sample is a physical transformation of the sample that separates the analytes into discrete portions that elute off of the chromatography column.

Figure 6:
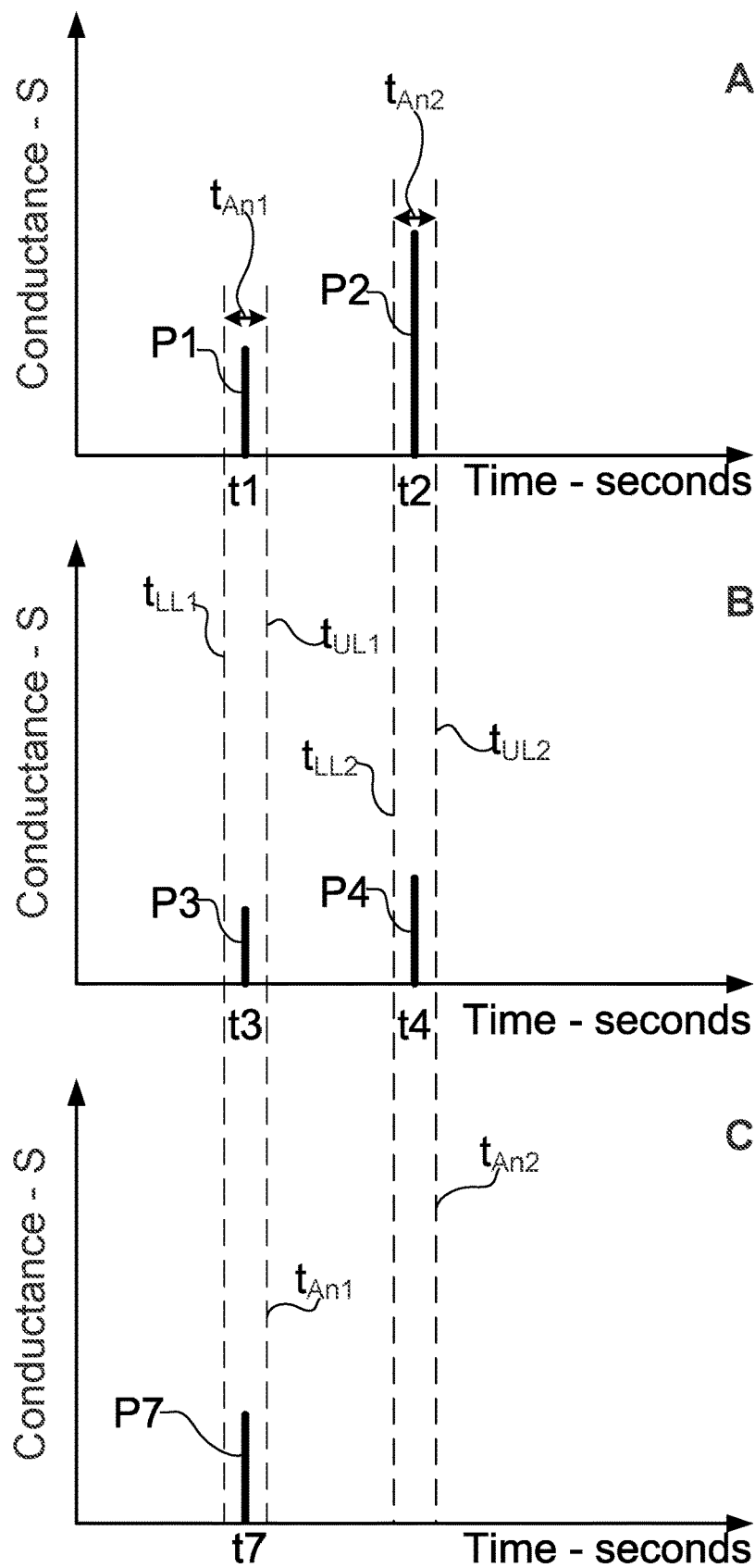
FIG. 6 shows a series of simulated chromatograms for a first diluted standard solution (A), a second diluted standard solution (B), and a sample containing a first analyte (C).

FIG. 6 illustrates an exemplary chromatogram A of the first diluted standard solution showing a detection of a first peak P1 and a second peak P2 that have a first retention time t1 and second retention time t2, respectively. Note that the peaks P1 and P2 are depicted as lines for simplicity and that the peaks can be of other shapes typically observed in chromatograms such as Gaussian.

In step 410, the method 400 includes automatically identifying whether the first peak corresponds to the first analyte or the second analyte. Similarly, step 412 automatically identifies whether the second peak corresponds to the first analyte or the second analyte. This automatic identification process is based on either an area or a height of the first peak and the second peak, and the first predetermined calibrant ratio. The first predetermined calibrant ratio [$2^{nd}$ Analyte/$1^{st}$ Analyte] can be multiplied by the first peak area to see if the product value corresponds to the second peak area, and if so, the first peak will correspond to the first analyte and the second peak to the second analyte. Similarly, the ratio value can be multiplied by the second peak area to see if the product value corresponds to the first peak area, and if so, the second peak will correspond to the first analyte and the first peak to the second analyte. It should be noted that as described herein that the analyte identity is calculated without using the retention times.

For example, the first peak area can be 0.25, the second peak area can be 0.5, and the first predetermined calibrant ratio can be 2:1 (acetate:chloride). In an embodiment, the first predetermined calibrant ratio×the first peak area equals the second peak area indicating that the first peak is chloride and the second peak is acetate (e.g., 2/1×0.25=0.5). In addition, the first predetermined calibrant ratio×the second peak area does not equal the first peak area indicating that the first peak is not acetate and the second peak is not chloride (e.g., 2/1×0.5≠0:25). In accordance with the exemplary chromatogram A of FIG. 6, the first peak P1 would be the first analyte chloride and the second peak P2 would be the second analyte acetate. Step 410 may include evaluate multiple permutations of pairs of peak areas using predetermined calibrant ratios to identify analytes. The automatic identification process of steps 410 and 412 is similar to filed U.S. patent application Ser. No. 13/834,883, filed on Mar. 15, 2013, which is hereby fully incorporated by reference herein.

In step 414, a first analyte time interval can be assigned based on one of the first retention time and second retention time that corresponds to the first analyte. Similarly, in step 416, a second analyte time interval can be assigned based on one of the first retention time and second retention time that corresponds to the second analyte. In an embodiment, a user can assign a first analyte time interval to the appropriate retention time corresponding to the first analyte. A software interface can be used so that a user can input a first analyte time interval that includes a first upper limit and a first lower limit where the retention time corresponding to the first analyte is in between the first upper limit and the first lower limit. A user may want to manually set the first analyte time interval to exclude co-eluting peaks. In another embodiment, the first upper limit can be the retention time corresponding to the first analyte plus a first predetermined proportion multiplied by this retention time and the first lower limit being the retention time corresponding to the first analyte minus the first predetermined proportion multiplied by this retention time. The second upper limit can be the retention time corresponding to the second analyte plus a second predetermined proportion multiplied by this retention time and the second lower limit being the retention time corresponding to the second analyte minus the second predetermined proportion multiplied by this retention time.

The first predetermined proportion and second predetermined proportion may each range from about 0.05 to about 0.2.

As an example, the retention time corresponding to the first analyte can be one minute and the first predetermined proportion can be 0.1. The first lower limit would be 0.9 minutes (1−(0.1×1)) and the first upper limit would be 1.1 minutes (1+(0.1×1)).

In another embodiment, the first upper limit and the first lower limit can be defined by having a fixed window such as 0.1 minutes. In this example, the window would be plus or minus 0.05 minutes of the first retention time.

As an example, where it is assumed that the first peak is the first analyte and the second peak is the second analyte, chromatogram A of FIG. 6 illustrates a first analyte time interval $t_{AN1}$ and a second analyte time interval $t_{AN2}$, which are based on the first retention time t1 and the second retention time t2, respectively. More particularly, the first analyte time interval $t_{AN1}$ can have a first upper limit $t_{UL1}$ and a first lower limit $t_{LL1}$, as illustrated in FIG. 6. The first upper limit $t_{UL1}$ can be the first retention time t1 plus a first predetermined proportion of the first retention time t1 and the first lower limit $t_{LL1}$ can be the first retention time t1 minus the first predetermined proportion of the first retention time t1. Similar to the first analyte time interval $t_{AN1}$, the second analyte time interval $t_{AN2}$ can have a second upper limit $t_{UL2}$ and a second lower limit $t_{LL2}$, as illustrated in FIG. 6. The second upper limit $t_{UL2}$ can be the second retention time t2 plus a second predetermined proportion of the second retention time t2 and the second lower limit $t_{LL2}$ can be the second retention time t2 minus the second predetermined proportion of the second retention time t2.

In step 418, a second diluted standard solution is formed by mixing the standard material and the diluent. The second diluted standard solution may include a first analyte having a third diluted calibrant concentration and a second analyte having a fourth diluted calibrant concentration. The first diluted standard solution is configured to have a first predetermined calibrant ratio. In an embodiment, the first diluted calibrant concentration is higher than the third diluted calibrant concentration for the first analyte, and the second diluted calibrant concentration is higher than the fourth diluted calibrant concentration for the second analyte.

Once the second diluted standard solution is prepared, it is injected into a chromatographic separator in step 420. The second diluted standard solution is separated in the chromatographic separator in step 422. A third peak and a fourth peak can be measured with a detector in step 424. The first peak and the second peak can have a third retention time and a fourth retention time, respectively.

As an example, where it is assumed that the first peak is the first analyte and the second peak is the second analyte, chromatogram B of FIG. 6 illustrates a chromatographic separation of the second diluted standard solution that results in a third peak P3 and a fourth peak P4 that have a third retention time t3 and a fourth analyte retention time t4, respectively.

Step 426 automatically identifies that the third peak corresponds to the first analyte where the third retention time falls within the first analyte time interval or the second analyte where the third retention time falls within the second analyte time interval. Similarly, step 428 automatically identifies that the fourth peak corresponds to the first analyte where the fourth retention time falls within the first analyte time interval or the second analyte where the fourth retention time falls within the second analyte time interval. It should be noted that identification steps 410 and 412 can be based on the first predetermined calibrant ratio whereas identification steps 426 and 428 can be based on first and second analyte time intervals. Applicant unexpectedly discovered that the combination of using a predetermined calibrant ratio (in steps 410 and 412) and then time intervals (in steps 426 and 428) provided an advantage when analyzing samples that contain at least one analyte that is weakly dissociated such as, for example, acetate. Weakly dissociated ions exist mainly in a non-ionized form. Under certain circumstances, a conductivity detector provides a non-linear response to analytes that are weakly dissociated. As a result, the predetermined calibrant ratio may not be constant for both the first and second diluted calibrant solutions. In contrast, samples that contain only fully or strongly dissociated analytes such as, for example, chloride have a constant predetermined calibrant ratio for both the first and second diluted calibrant solution. Strongly dissociated ions exist mainly in an ionized form. When all of the analytes are fully dissociated, steps 426 and 428 can be similar to steps 410 and 412 where the identification is also based on the predetermined calibrant ratio.

As an example, where it is assumed that the first peak is the first analyte and the second peak is the second analyte, chromatogram B of FIG. 6 illustrates that the third retention time t3 falls within the first analyte time interval $t_{AN1}$ and that the fourth retention time t4 falls within the second analyte time interval $t_{AN2}$. Note that a retention time falls within an analyte time interval where the retention time is greater than $t_{LL}$ and less than the $t_{UL}$.

Step 430 automatically calculates a first calibration equation for the first analyte based on an area or a height of two of the automatically identified peaks that correspond to the first analyte, the first diluted calibrant concentration, and the third diluted calibrant concentration. The two peaks can be selected from the group consisting of the first peak, the second peak, the third peak, and the fourth peak (measured in steps 408 and 424). Similarly, step 432 automatically calculates a second calibration equation for the second analyte based on an area or a height of two of the automatically identified peaks that correspond to the second analyte, the second diluted calibrant concentration, and the fourth diluted calibrant concentration. The two peaks can be selected from the group consisting of the first peak, the second peak, the third peak, and the fourth peak (measured in steps 408 and 424).

In an embodiment, the first and second calibration equation can be calculated using linear regression. For this linear fit, the first calibration equation includes a first calibration slope and a first y-intercept and the second calibration equation includes a second calibration slope and second y-intercept.

For the situation where the calibration results in a non-linear response, the first and second calibration equation can be a first and second polynomial equation. A third calibration point is typically needed for calculating a polynomial equation so method 400 can further include forming another diluted standard solution by mixing a standard material and a diluent.

In an embodiment, method 400 may include a feature where a user can input the relevant concentration range of the analyte to be measured. This inputting of the concentration range allows the method to automatically set the appropriate concentrations for calibrating the system. For instance, calibration concentrations are typically slightly less than the lowest expected analyte concentration and slightly higher than the highest expected analyte concentration. Before forming the first diluted standard solution and the second diluted standard solution in steps 402 and 418, a user can input a first concentration range into a user interface of a chromatography software system. The concentration range represents the lowest and highest analyte concentrations expected to be found by the user in a sample containing the analyte. This inputted first concentration range is received by the user interface software. The first concentration range includes a lower first analyte concentration and an upper first analyte concentration.

The first diluted calibrant concentration can be automatically calculated based on the upper first analyte concentration. Next, a) a first flow rate or a first pump duration time for the first aliquot and b) a second flow rate or a second pump duration time for the second aliquot can be automatically set to form the automatically calculated first diluted calibrant concentration.

Similarly, the third diluted calibrant concentration can be automatically calculated the based on the lower first analyte concentration. Next, c) a third flow rate or a third pump duration time for a third aliquot and d) a fourth flow rate or a fourth pump duration time for the fourth aliquot can be automatically set to form the automatically calculated third diluted calibrant concentration.

Figure 5:
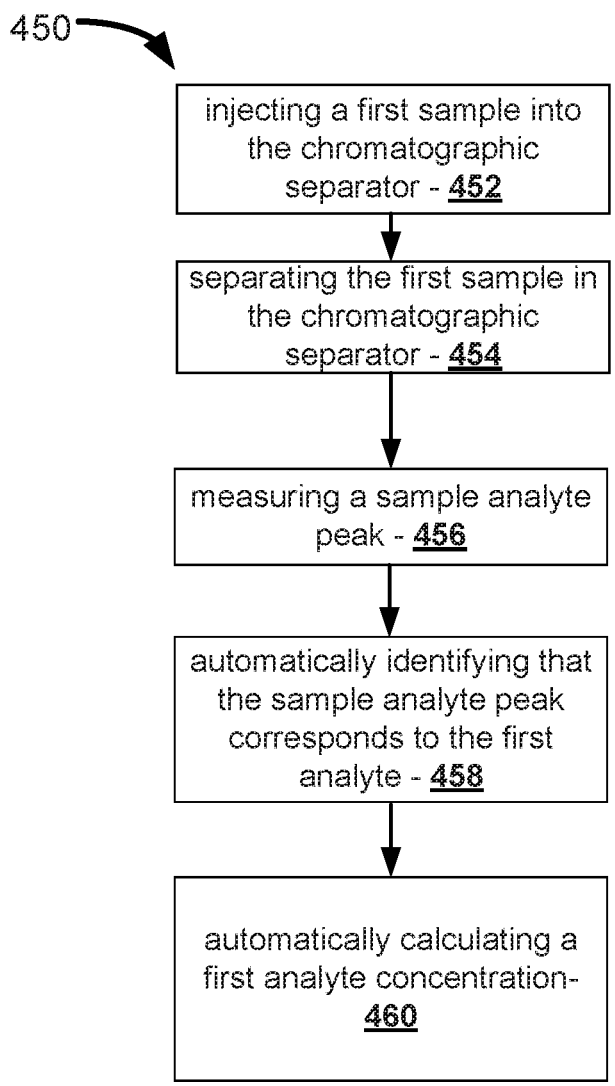
FIG. 5 is a flow chart illustrating an automatic method of automatically identifying and quantifying the analyte in a chromatography system that has been calibrated.

Now that automatic calibration processes have been described, the following will describe methods for analyzing a sample. In an embodiment, a method 450 includes a step 452 of injecting a first sample into the chromatographic separator, as shown in FIG. 5. The first sample includes at least a first analyte. The first sample is separated in the chromatographic separator as shown in step 454. A sample analyte peak is measured with the detector as shown in step 456. The sample analyte peak may also be referred to as a seventh peak that has a seventh retention time. Step 458 automatically identifies that the seventh peak corresponds to the first analyte where the seventh retention time falls within the first analyte time interval. Step 460 automatically calculates a first analyte concentration of the first sample based on an area or a height of the seventh peak and the first calibration equation.

As an example, chromatogram C of FIG. 6 illustrates a chromatogram of a first sample that results in a seventh peak, having a seventh retention time t7. The seventh retention time t7 falls within the first analyte time interval $t_{AN1}$ indicating that the sample includes the first analyte. The height or area of the seventh peak can be used to calculate the concentration of the first analyte using the first calibration equation.

Under certain circumstances, the automatically calculated first analyte concentration can be less than the lower first analyte concentration of the first concentration range. In such a case, a feedback control mechanism can be implemented where the previously set lower first analyte concentration is adjusted to be lower than the automatically calculated first analyte concentration. In turn, the calibration is redone with a fourth diluted standard solution. A seventh diluted calibrant concentration can be calculated for the first analyte that is less than the automatically calculated first analyte concentration. The fourth diluted standard solution can be formed by mixing the standard solution and the diluent. The fourth diluted standard solution includes a first analyte having the seventh diluted calibrant concentration. The fourth diluted standard solution can be injected into the chromatographic separator. The fourth diluted standard solution can be separated in the chromatographic separator. An eighth peak can be measured, with the detector, that has an eighth retention time. Automatically identifying that the eighth peak corresponds to the first analyte where the eighth retention time falls within the first analyte time interval. Automatically calculating an adjusted first calibration equation for the first analyte based on an area or a height of the eighth peak corresponding to the new lower first analyte concentration and at least one peak of the first, second, third, and fourth peaks that corresponds to the first analyte, and the seventh diluted calibrant concentration and at least one of the first, second, third, and fourth diluted calibrant concentrations that corresponds to the first analyte.

Under certain circumstances, the automatically calculated first analyte concentration can be greater than the upper first analyte concentration of the first concentration range. In such a case, a feedback control mechanism can be implemented where the previously set upper first analyte concentration is adjusted to be higher than the automatically calculated first analyte concentration. In turn, the calibration is redone with a fifth diluted standard solution. An eighth diluted calibrant concentration can be calculated for the first analyte that is greater than the automatically calculated first analyte concentration. The fifth diluted standard solution can be formed by mixing the standard solution and the diluent. The fifth diluted standard solution includes a first analyte having an eighth diluted calibrant concentration. The fifth diluted standard solution can be injected into the chromatographic separator. The fifth diluted standard solution can be separated in the chromatographic separator. A ninth peak can be measured, with the detector, that has a ninth retention time. Automatically identifying that the ninth peak corresponds to the first analyte where the ninth retention time falls within the first analyte time interval. Automatically calculating an adjusted first calibration equation for the first analyte based on an area or a height of the ninth peak corresponding to the new upper first analyte concentration and at least one peak of the first, second, third, and fourth peaks that corresponds to the first analyte, and the eight diluted calibrant concentration and at least one of the first, second, third, and fourth diluted calibrant concentrations that corresponds to the first analyte.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of calibrating a chromatography system, the method comprising:
   forming a first diluted standard solution by mixing a standard material and a diluent, the first diluted standard solution comprising:
   a first analyte having a first diluted calibrant concentration, and a second analyte having a second diluted calibrant concentration,
in which the first diluted standard solution is configured to have a first predetermined calibrant ratio;
injecting the first diluted standard solution into a chromatographic separator;
separating the first diluted standard solution in the chromatographic separator;
measuring, with a detector, a first peak and a second peak that have a first retention time and a second retention time, respectively; and
automatically identifying
whether the first peak corresponds to the first analyte or the second analyte, and
whether the second peak corresponds to the first analyte or the second analyte, based on
either an area or a height of the first peak and the second peak, and
the first predetermined calibrant ratio;
forming a second diluted standard solution by mixing the standard material and the diluent, the second diluted standard solution comprising:
the first analyte having a third diluted calibrant concentration, and
the second analyte having a fourth diluted calibrant concentration;
injecting the second diluted standard solution into the chromatographic separator;
separating the second diluted standard solution in the chromatographic separator;
measuring, with the detector, a third peak and a fourth peak that have a third retention time and a fourth retention time, respectively;
automatically identifying
whether the third peak corresponds to the first analyte or the second analyte, and
whether the fourth peak corresponds to the first analyte or the second analyte, based on
either an area or a height of the third peak and the fourth peak, and
the first predetermined calibrant ratio;
automatically calculating a first calibration equation for the first analyte based on
an area or a height of two of the automatically identified peaks that correspond to the first analyte, the two peaks selected from the group consisting of the first peak, the second peak, the third peak, and the fourth peak, and
the first and third diluted calibrant concentrations; and
automatically calculating a second calibration equation for the second analyte based on
an area or a height of two of the automatically identified peaks that correspond to the second analyte, the two peaks selected from the group consisting of the first peak, the second peak, the third peak, and the fourth peak, and
the second and fourth diluted calibrant concentrations.

2. The method of claim 1, in which the first calibration equation comprises a first calibration slope and a first y-intercept and the second calibration equation comprises a second calibration slope and a second y-intercept.

3. The method of claim 1 further comprising:
assigning a first analyte time interval based on one of the first retention time and the second retention time that corresponds to the first analyte;
assigning a second analyte time interval based on one of the first retention time and the second retention time that corresponds to the second analyte;
injecting a first sample into the chromatographic separator, the first sample comprising at least a first analyte;
separating the first sample in the chromatographic separator;
measuring, with the detector, a fifth peak that has a fifth retention time;
automatically identifying that the fifth peak corresponds to the first analyte where the fifth retention time falls within the first analyte time interval; and
automatically calculating a first analyte concentration of the first sample based on an area or a height of the fifth peak and the first calibration equation.

4. The method of claim 3 further comprising:
calculating a fifth diluted calibrant concentration for the first analyte that is less than the automatically calculated first analyte concentration when the automatically calculated first analyte concentration is less than a lower first analyte concentration of a first concentration range;
forming a third diluted standard solution by mixing the standard solution and the diluent, the third diluted standard solution comprising a first analyte having the fifth diluted calibrant concentration;
injecting the third diluted standard solution into the chromatographic separator;
separating the third diluted standard solution in the chromatographic separator;
measuring, with the detector, a sixth peak that has a sixth retention time;
automatically identifying that the sixth peak corresponds to the first analyte where the sixth retention time falls within the first analyte time interval; and
automatically calculating an adjusted first calibration equation for the first analyte based on
an area or a height of the sixth peak and at least one peak of the first, second, third, and fourth peaks that corresponds to the first analyte, and
the fifth diluted calibrant concentration and at least one of the first, second, third, and fourth diluted calibrant concentrations that corresponds to the first analyte.

5. The method of claim 1, in which the standard material includes a standard solution, the forming of the first diluted standard solution comprises:
pumping a first aliquot of the standard solution into a junction, the standard solution comprising:
the first analyte having the first calibrant concentration, and
the second analyte having the second calibrant concentration;
pumping a second aliquot of the diluent into the junction; and
mixing the first aliquot and the second aliquot to form the first diluted standard solution; and the forming of the second diluted standard solution comprises:
pumping a third aliquot of the standard solution into the junction;
pumping a fourth aliquot of the diluent into the junction; and
mixing the third aliquot and fourth aliquot to form the second diluted standard solution.

6. The method of claim 5 further comprising:
before forming the first diluted standard solution and the second diluted standard solution, receiving a first concentration range for the first analyte, the first concentration range including a lower first analyte concentration and an upper first analyte concentration;

automatically calculating the first diluted calibrant concentration based on the upper first analyte concentration;

automatically setting
- a first flow rate or a first pump duration time for the first aliquot and
- a second flow rate or a second pump duration time for the second aliquot to form the automatically calculated first diluted calibrant concentration;

automatically calculating the third diluted calibrant concentration based on the lower first analyte concentration; and automatically setting
- a third flow rate or a third pump duration time for the third aliquot and
- a fourth flow rate or a fourth pump duration time for the fourth aliquot to form the automatically calculated third diluted calibrant concentration.

7. The method of claim 6, in which the junction comprises a T-junction.

8. The method of claim 7, in which the mixing occurs in a mixing chamber downstream of the T-junction.

* * * * *